United States Patent

Karl et al.

[11] Patent Number: 5,786,498
[45] Date of Patent: Jul. 28, 1998

[54] RESOLUTION OF RACEMATES OF 2-ARYL-2-ALKYL-ω-ALKYLAMINOALKANE-NITRILES

[75] Inventors: Ulrich Karl, Ludwigshafen; Werner Seitz, Plankstadt, both of Germany

[73] Assignee: BASF Aktiengesellschaft, Ludwigshafen, Germany

[21] Appl. No.: 860,664

[22] PCT Filed: Jan. 20, 1996

[86] PCT No.: PCT/EP96/00236

§ 371 Date: Jul. 7, 1997

§ 102(e) Date: Jul. 7, 1997

[87] PCT Pub. No.: WO96/23764

PCT Pub. Date: Aug. 8, 1996

[30] Foreign Application Priority Data

Jan. 31, 1995 [DE] Germany .................. 195 02 967.4

[51] Int. Cl.⁶ .................................................. C07C 253/00
[52] U.S. Cl. .................................................. 558/334
[58] Field of Search .................................................. 558/354

[56] References Cited

U.S. PATENT DOCUMENTS 5,457,224  10/1995  Ehrmann et al. .

FOREIGN PATENT DOCUMENTS

| 271 013 | 6/1988 | European Pat. Off. . |
| 357 575 | 3/1990 | European Pat. Off. . |
| 20 59 985 | 6/1972 | Germany . |
| 37 23 684 | 1/1989 | Germany . |
| 42 03 547 | 8/1993 | Germany . |
| 1 377 209 | 12/1974 | United Kingdom . |
| 92/07821 | 5/1992 | WIPO . |
| 95/09150 | 4/1995 | WIPO . |

OTHER PUBLICATIONS

Helvetica Chimica Acta, vol. 58, 7 (1975), 2050–2060.
J. Org. Chem. (1987), 52, 1309–1315.
Monatsheft fur Chem. 122, 841–848 (1991).

Primary Examiner—Robert W. Ramsuer
Assistant Examiner—Joseph Murray
Attorney, Agent, or Firm—Keil & Weinkauf

[57] ABSTRACT

A process for resolving the racemates of phenylacetonitriles of the formula I

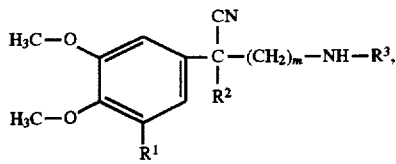

where $R^1$, $R^2$, $R^3$ and m have the meanings stated in the description is described. The process comprises dissolving the racemates I in a polar solvent, adding from 0.5 to 1.0 mol of optically active camphorsulfonic acid per mol of compound I, heating to 40°–100° C., allowing to cool and liberating the optically active phenylacetonitrile I from the salt obtained in this way.

1 Claim, No Drawings

RESOLUTION OF RACEMATES OF 2-ARYL-2-ALKYL-ω-ALKYLAMINOALKANE-NITRILES

This application is a 371 of PCT/EP96/00236 filed on Jan. 20, 1996.

Phenylacetonitriles which have various substituents on the phenyl group and have a basic side chain have found use as effective pharmaceutical agents. Thus, of the phenylacetonitriles of the formula II with basic substituents described in DE 11 54 810, verapamil (II, R=H) and gallopamil (II, R=OCH$_3$) are of proven use in the treatment of coronary heart disease and high blood pressure.

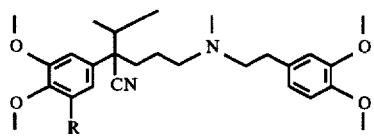

II

EP 0 271 013 describes phenylacetonitriles which have an aliphatic side chain in place of the dimethoxyphenylethyl radical on the nitrogen as agents for cardiovascular and asthmatic disorders.

The substituted phenylacetonitriles have a chiral carbon atom so that, in the absence of other centers of chirality, they form two enantiomers (optical antipodes). Conventional chemical syntheses starting from achiral substances produce the two enantiomers in equal amounts so that a racemate results.

It is known of verapamil and gallopamil that there are distinct quantitative differences between the enantiomers in their pharmacodynamics and -kinetics (M. Raschack, Naunyn-Schmiedeberg's Arch. Pharmacol. 294 (1976) 285; M. Eichelbaum et al., Br. J. Clin. Pharmacol. 17 (1984) 453). Thus, the levorotatory enantiomer is a much more effective coronary dilator whereas the dextrorotatory antipode has been used to break resistance in malaria and tumor therapy.

The preparation of optically active phenylacetonitriles is therefore of great importance.

However, this preparation is very difficult: when chiral catalysts are used in the synthesis of verapamil, the maximum enantiomeric excess which could be achieved was only 10%, ie. a 55:45 ratio of enantiomers (H. Brunner and H. Zintl, Monatsh. Chemie 122 (1991) 841–848). The enantiomeric excesses provided by other chiral catalysts are also completely inadequate.

The stereospecific synthesis of the enantiomers of verapamil and gallopamil described by L. J. Theodore and W. L. Nelson (J. Org. Chem. 52 (1987) 1309–1315) starts from the stereoisomeric lactic acids and cannot be carried out on the industrial scale because of the large number of reaction stages and complicated chemical modifications of functionalities.

Methods of racemate resolution have been published relatively frequently. There is a special case in WO 92/07821, where resolution of a racemate of the phenylacetonitrile moiety takes place by linkage to optically active β-methylaminotetralin, which becomes part of the agent, and fractional crystallization of the diastereomers:

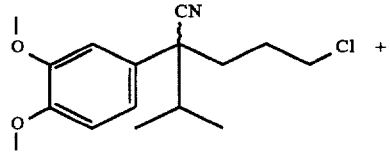

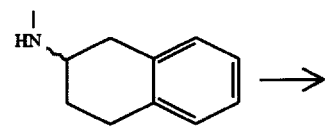

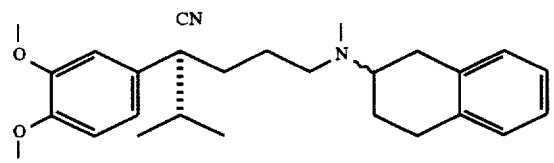

More widely applicable is the intermediate formation of diastereomeric salts which can be fractionated by crystallization or chromatography, and liberation of the required optically active product from the salt.

The difficulty of racemate resolution is evident from the fact that it was for a long time not possible to resolve the final product itself, ie. the agent or one of its basic precursors via which the syntheses normally take place, on the contrary there was racemate resolution of the carboxy derivatives III or IV, whose conversion into the required product verapamil requires additional synthetic steps, with chiral bases.

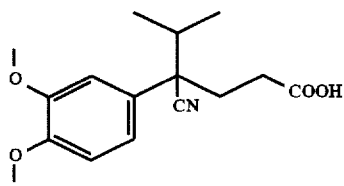

III

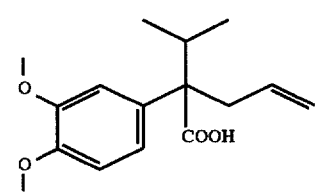

IV

Brucine is used to resolve III (DE 2059 985), which is disadvantageous because of the extreme toxicity and high price of brucine. Although IV can be resolved with cinchonidine, it must be modified at two functionalities in order to obtain the desired product, which is difficult to carry out industrially (H. Ramuz, Helv. Chim. Acta 58 (1975) 2050–2060).

The chiral precursors V and VI used in Examples 6 and 7 in EP 0271 013 were prepared by the method described in DE 2059 985.

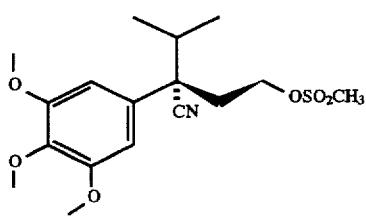

V

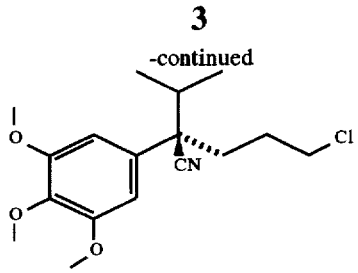

Only later were processes described for resolving the racemate of verapamil free base. (R)- or (S)-1,1'-binaphthyl-2,2'-diyl hydrogen phosphate is used as resolving acid in DE-A 3 723 684, but the preparation of this is extremely elaborate and it is not available in industrial quantities. DE-A 4 203 547 uses one to two equivalents of O,O'-dibenzoyl- or O,O'-di-p-toluoyltartaric acid, both of which are very costly and are readily hydrolyzed during the liberation of verapamil and are thus lost.

It was surprising, especially in view of the statement by H. Ramuz (Helv. Chim. Acta 58 (1975) 2050) that camphorsulfonic acid is unsuitable for resolving verapamil racemate, that phenylacetonitriles with basic substituents can easily be resolved to optical antipodes of high enantiomeric purity using camphorsulfonic acid.

The invention relates to a process for resolving the racemates of 2-aryl-2-alkyl-(ω-alkylaminoalkanenitriles of the formula I

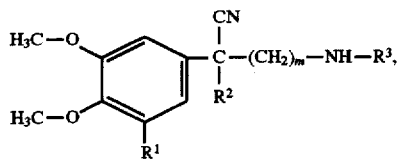

where
$R^1$ is hydrogen or methoxy,
$R^2$ and $R^3$, which are identical or different, are $C_{1-4}$-alkyl, and
m is 2 or 3,
in a conventional way, wherein optically active camphorsulfonic acid is used as resolving reagent.

$C_{1-4}$-Alkyl groups which may be mentioned are the following: methyl, ethyl, n-propyl, isopropyl, cyclopropyl, n-butyl, isobutyl, sec-butyl, tert-butyl.

The process according to the invention is preferably carried out in the following way: 1 equivalent of racemic I is introduced into an alcohol such as methanol, ethanol, n-propanol, iso-propanol, glycol, diglycol or a mixture of the alcohols or a mixture of an alcohol with acetone or ethyl acetate (preferably isopropanol), and 0.5–1 (preferably 0.75) equivalent of camphorsulfonic acid monohydrate is added. The mixture is then heated to from 40° C. to 100° C. or to the boiling point of the solvent (preferably 60° C.). On cooling, the diastereomeric camphorsulfonate of the compound I crystallizes out: (S)-(+)-camphorsulfonic acid precipitates as salt with (S)-I, (R)-(–)-camphorsulfonic acid precipitates with (R)-I.

The salt is recrystallized once, preferably from the solvent or solvent mixture previously used.

To liberate optically active I, the salt is dissolved in dilute alkaline solution (eg. sodium or potassium hydroxide solution or potassium carbonate solution) and extracted with a water-immiscible solvent (eg. ethyl acetate, MTBE (=methyl tert-butyl ether), dichloromethane). The optically active compound I can be precipitated from these solutions or immediately reacted further therein.

The process according to the invention is extremely favorable because camphorsulfonic acid is very cheap and can also be obtained in industrial quantities and because the resulting intermediates of the formula I allow a large number of agents such as verapamil, gallopamil and the compounds described in EP 0 271 013 to be prepared.

The racemic starting compounds of the formula VI used for the process according to the invention can be prepared as shown in the following scheme:

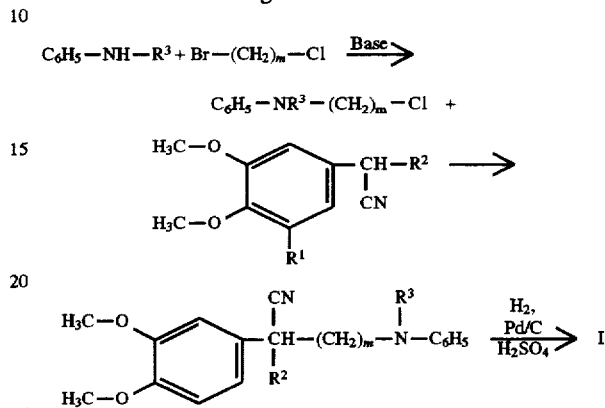

The following examples are intended to illustrate the process according to the invention without restricting it.

EXAMPLE 1

(S)-(–)-5-(N-methylamino)-2-(1-methylethyl)-2-(3,4,5-trimethoxyphenyl)pentanenitrile [I, $R^1$=OCH$_3$, $R^2$=CH(CH$_3$)$_2$, $R^3$=CH$_3$]

95.4 kg (297.8 mol) of racemic 5-(N-methylamino)-2-(1-methylethyl)-2-(3,4,5-trimethoxyphenyl)pentanenitrile were introduced together with 55.9 kg (223.4 mol) of (S)-(+)-camphor-10-sulfonic acid monohydrate into 200 l of isopropanol.

The mixture was heated to an internal temperature of 60° C., resulting in a clear solution. It was then slowly cooled. Crystallization started after seeding with the salt at 30° to 35° C. The mixture was cooled to 20° C. with stirring. The precipitate was filtered off, washed with 50 l of isopropanol and recrystallized from 300 l of isopropanol.

The dried diastereomeric salt was dissolved in 300 l of water containing 30 kg of 50% strength sodium hydroxide solution and extracted twice with 100 l of methyl t-butyl ether each time.

Yield: 30.9 kg (96.5 mol) ≙66% of theory $[\alpha]_D^{20}$–17.8° (c=1, toluene).

The product is in the form of an oil. The hydrochloride melts at 192–194 ° C., $[\alpha]_D^{20}$–9.0° (c=1, ethanol abs.).

EXAMPLE 2

(R)-(+)-5-N-Methylamino-2-(1-methylethyl)-2-(3,4,5-trimethoxyphenyl)pentanenitrile The dextrorotatory enantiomer is obtained on use of (R)-(–)-camphor-10-sulfonic acid monohydrate as resolving acid as in Example 1. The pure base has a specific rotation of $[\alpha]_D^{20}$=+17.8° (c=10 mg/ml, toluene).

The hydrochloride melts at 192–194° C., $[\alpha]_D^{20}$=9.1° (c=1, ethanol abs.).

EXAMPLE 3

(S)-(−)-5-(N-Methylamino)-2-(1-methylethyl)-2-(3,4-dimethoxyphenyl)pentanenitrile The substance was prepared as in Example 1. The specific rotation of the free base is $[\alpha]_D^{20} = -5.0°$ (c=1, ethanol abs.). The hydrochloride melts at 172°–173 °C.

EXAMPLE 4

(R)-(+)-5-N-Methylamino-2-(1-methylethyl)-2-(3,4-dimethoxyphenyl) pentanenitrile The substance was prepared as in Example 2. The base is in the form of an oil and has a specific rotation of $[\alpha]_D^{20} = +5°$ (c=1, ethanol abs.). The hydrochloride melts at 172°–175° C.

We claim:

1. A process for resolving the racemates of 2-aryl-2-alkyl-ω-alkylaminoalkanenitriles of the formula I

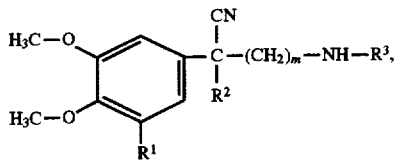

where $R^1$ is hydrogen or methoxy, $R^2$ and $R^3$, which are identical or different, are $C_{1-4}$-alkyl, and m is 2 or 3, in a conventional way, wherein optically active camphorsulfonic acid is used as resolving reagent.

* * * * *